United States Patent [19]
Corella

[11] Patent Number: 5,794,776
[45] Date of Patent: Aug. 18, 1998

[54] INSTRUMENTATION, SYSTEM, METHOD AND PACKAGE FOR PACKAGING FLACCID FILAMENTS

[76] Inventor: Arthur P. Corella, 8166 Vanscoy, North Hollywood, Calif. 91602

[21] Appl. No.: 861,461

[22] Filed: May 22, 1997

Related U.S. Application Data

[63] Continuation of Ser. No. 589,862, Jan. 22, 1996, abandoned.

[51] Int. Cl.$^6$ ..................................................... A61C 15/04
[52] U.S. Cl. ......................... 206/388; 206/63.3; 206/63.5; 53/554
[58] Field of Search ..................... 206/388, 63.3, 206/65.5, 390, 409, 484; 383/107, 108; 53/28, 79, 450, 477, 550, 554, 451, 591; 156/73.1, 439

[56] References Cited

U.S. PATENT DOCUMENTS

| | | | |
|---|---|---|---|
| 2,965,225 | 12/1960 | Zoller et al. | 206/63.3 |
| 2,970,414 | 2/1961 | Rohdin . | |
| 3,204,760 | 9/1965 | Whiteford | 206/484 |
| 3,220,161 | 11/1965 | Lohse et al. | 53/477 |
| 3,325,969 | 6/1967 | Bemiss et al. . | |
| 3,477,194 | 11/1969 | Corrsin . | |
| 3,605,374 | 9/1971 | Mueller et al. | 53/477 |
| 3,608,566 | 9/1971 | Storandt | 206/63.5 |
| 3,651,615 | 3/1972 | Bohner et al. | 156/73.1 |
| 4,014,433 | 3/1977 | Cerwin | 206/484 |
| 4,081,942 | 4/1978 | Johnson | 53/79 |
| 4,106,262 | 8/1978 | Atenianus | 53/28 |
| 4,183,964 | 1/1980 | Vinokur | 53/450 |
| 4,257,838 | 3/1981 | Asp et al. | 156/439 |
| 4,299,075 | 11/1981 | Gram | 53/550 |
| 4,579,221 | 4/1986 | Corella . | |
| 4,662,978 | 5/1987 | Oki | 53/477 |
| 4,693,365 | 9/1987 | Corella . | |
| 4,712,572 | 12/1987 | Hovel, III | 206/388 |
| 5,159,366 | 10/1992 | Gell, Jr. | 206/811 |
| 5,322,077 | 6/1994 | Corella | 206/388 |
| 5,549,201 | 8/1996 | Braude | 206/388 |

FOREIGN PATENT DOCUMENTS

2035201  6/1980  United Kingdom ..................... 53/202

Primary Examiner—Paul T. Sewell
Assistant Examiner—Luan K. Bui
Attorney, Agent, or Firm—Donald Diamond

[57] ABSTRACT

An improved instrumentation and method for manufacturing from film wrapping material hermetically sealed packages containing an untangled, unknotted segment of flaccid filament, and packages produced by the instrumentation and method. Instrumentation improvements include a gripper assembly for impeding uncut filament from backing up during filament loading in the course of package construction, an improved piston also impeding filament backup and facilitating deposition of a filament segment into an open package compartment, and a sealing mechanism for superimposing a seal over the top and bottom package seals.

3 Claims, 13 Drawing Sheets

INSTRUMENTATION, SYSTEM, METHOD AND PACKAGE FOR PACKAGING FLACCID FILAMENTS

This application is a continuation of application Ser. No. 08/589,862, filed Jan. 22, 1996, now abandoned.

BACKGROUND OF THE INVENTION

1. Field of the Invention

The present invention relates to instrumentation for packaging, in sealed packages, segments of flaccid filament cut from an uncut supply, one or more segments per package, with the ends thereof disposed within the package seal, so that each segment has a common predetermined length and is deposited and can be withdrawn in an untangled and unknotted condition. The invention further relates to dispensing packages thus produced which are hermetically sealed, particularly packages containing filaments such as dental floss.

2. Description of the Related Art

My prior patent, U.S. Pat. No. 4,579,221 ("'221"), which is incorporated herein by reference in its entirety, discloses an instrumentation which packages flaccid items such as filaments and thin wires within sealed packages so that an item can be packaged and eventually withdrawn in an untangled and unknotted condition. The packages are formed in a continuous manner from continuous lengths of the wrapping material and the flaccid item. The material is taken either from tubular stock formed generally as a sheath or from a pair of appropriately sealed sheets to provide a compartment with opposed sidewalls, an open top, and a sealed bottom, wherein one end of the flaccid item is disposed within the sealed bottom. An additional amount of the flaccid item is positively fed and deposited into the compartment in an untangled and unknotted condition by a feeding mechanism. The compartment is then sealed at its open end so as to enclose the other end of the flaccid item, and the completed package cut from the stock.

The instrumentation uses basically standard packaging machinery which is modified with the addition of filament feeding devices and relative movements among the several mechanical elements. Specifically, the feeding mechanism when the flaccid item is a filament such as dental floss includes a metallic feed tube concentrically placed and slidable within a metallic tubular mandrel. The feed tube is moved in sequential operations relative to the mandrel and with respect to compartment-holding and -sealing mechanisms so that the packages are appropriately formed. A piston fabricated from polytetrafluoroethylene or an equivalent composition circumferentially encloses the feed tube near its lower end so that the segment of filament extending from the feed tube end is bunched-up and deposited into an open compartment end as the piston travels downwardly. Because movement of the filament within the feed tube is unconstrained other than by the tube inner wall, this arrangement does not allow accurate control of the length of segment deposited and is highly susceptible to the filament backing-up in the feed tube.

My prior patent, U.S. Pat. No. 4,693,365 ("'365"), which is incorporated herein by reference in its entirety, discloses an improved feed tube/piston design wherein the piston extends downwardly from the tube end and a properly dimensioned exit hole is provided in the piston through which the filament is threaded. The hole is smaller than the inside dimension of the tube and is sized so as to exert a frictional hold on the filament as the segment extending beyond the piston is pushed by the piston into the compartment. A second improvement vis-a-vis the '221 instrumentation is a sequence of mechanical movements whereby a filament segment is straightened before being deposited. Even with these improvements, filaments which are thin and relatively stiff tend to push back up the exit hole into the piston as the feed tube/piston goes down, so that instead of a desired predetermined uniform length, smaller, randomly variable lengths are deposited.

The standard packaging machinery utilized in the '221 and '365 patents includes a vertical sealing mechanism used to form opposed side seals and a horizontal sealing mechanism used to simultaneously form the bottom and top seals of successive packages. Because efficient utilization of this machinery requires that horizontal seals be formed in less time than vertical seals so that the horizontal seals are less securely bonded, single horizontal seals generally are ineffective in preventing ambient oxygen from "wicking" into a sealed package and causing oxidative deterioration of susceptible contents. Consequently, hermetically sealed packages essential to preserve the integrity of filament products such as dental floss coated and/or impregnated with a flavoring or medication cannot be reliably formed using single top and bottom seals.

Thus, there remains a need for an instrumentation capable of packaging uniform unknotted and untangled lengths of any of a variety of filaments including those that are thin and relatively stiff. And there further remains a need for a method and instrumentation for forming hermetically sealed packages containing filaments subject to oxidation.

OBJECTS OF THE INVENTION

Accordingly, it is an object of the present invention to provide a packaging instrumentation which enables repetitively depositing a predetermined length of untangled and unknotted filament into an open-ended compartment without significant limitation with respect to physical and chemical properties.

Another object of the invention is to provide a packaging instrumentation that can be easily modified to accommodate a filament having a diameter within a commercially useful range of diameters.

A further object of the invention is to provide an instrumentation that is simple and reliable to operate.

Yet another object of the invention is to provide an instrumentation capable of forming hermetically sealed packages enclosing an untangled and unknotted length of filament or wire.

A further object of the invention is to provide a method for forming hermetically sealed packages which enables high speed production.

A still further object of the invention is to provide hermetically sealed packages that are simple, reliable and inexpensive to produce.

Other objects of the invention will become evident when the following description is considered with the accompanying drawings.

SUMMARY OF THE INVENTION

These and other objects of the invention are achieved by modifying the '365 instrumentation and appropriately modifying the process steps performed. The '365 instrumentation manufactures from continuous supplies of film sheeting material and uncut flaccid filament, sealed packages containing untangled and unknotted filament, and includes a vertical sealing mechanism which forms side seals in the material, a holder mechanism coupled to the vertical sealing mechanism so that the two mechanisms move up and down in unison, a horizontal sealing mechanism disposed between the vertical sealing mechanism and the holder mechanism which simultaneously forms the top and bottom seals of two contiguous packages, a feed tube which is slidable up and down within a mandrel, a piston attached to the feed tube which includes an exit hole through which filament feeds, and a holding-and cutting-mechanism disposed below the holder mechanism. The coupled vertical sealing and holder mechanisms are at their uppermost position when the feed tube and piston are at their lowermost position, and vice versa. The improvement includes means for preventing the filament from backing up into the piston and feed tube, means for preventing filament accumulating near the exit hole from wedging between the piston and mandrel, and means for superimposing a seal over the top and bottom seals of contiguous packages.

Specifically, the means for preventing the filament from backing up into the piston and feed tube includes a gripper assembly connected to and moving vertically in unison with the feed tube and piston, and a first improved piston including a tapered bore terminating in an exit hole, an upper portion tapered so that only its lowermost portion contacts the mandrel, and a thinner tapered lower portion. The bore tapers downwardly from a diameter about that of the feed tube inner diameter, to a diameter, for example, about 0.010-inch larger than the filament diameter, resulting in frictional resistance between a filament segment traversing the bore and the lower bore surface and exit hole. The gripper clamps the filament while the feed tube and piston travel downwardly so that a relatively taut, stiff, thin filament reacting according to Newton's third law against the downward piston force cannot migrate back up the feed tube. The filament segment extending beyond the exit hole tends to curl in a spiral around the piston lower portion and so can easily be pulled off by the holder as the piston nears the end of its downward stroke. As the piston moves downward the gripper moves with it, clamping the filament to prevent any upward movement within the piston and feed tube.

Specifically, the means for preventing filament from wedging between the piston and mandrel includes a circular groove transected by a plurality of radial grooves in the planar annular surface of the lower end of the piston upper portion. As the piston moves up and down within the mandrel, the grooves allow the piston portion contacting the mandrel to flex slightly, thereby mitigating erosion which over time would wear down the piston surface, creating an annular crevice in which filament exiting the hole would tend to lodge. Alternatively, a second improved piston can be used which has a tapered bore terminating in an exit hole within a unitary body tapered so that only its lowermost portion contacts the mandrel. The planar surface of the piston lower end has a circular groove transected by a plurality of radial grooves, and the bore tapers downwardly from a diameter about that of the feed tube inner diameter, to a diameter, for example, about 0.010-inch larger than the filament diameter.

Specifically, the means for superimposing a seal over the top and bottom seals of contiguous packages includes a second horizontal sealing mechanism disposed between the holder and holding-and-cutting mechanisms. The mechanism includes opposed first and second platens each having a smooth or, alternatively, a corrugated ("tongue-and-groove") vertical surface. As the junction region of each pair of contiguous packages (which includes the top seal of the leading package and the bottom seal of the trailing package) passes between the opened platens, the platens are closed while heat is applied, thus forming a seal covering the top and bottom seals.

A more complete understanding of the present invention and other objects, aspects and advantages thereof will be gained from a consideration of the following description of the preferred embodiment read in conjunction with the accompanying drawings provided herein.

DESCRIPTION OF THE PREFERRED EMBODIMENT

While the present invention is open to various modifications and alternative constructions, the preferred instrumentation embodiment shown in the drawings will be described herein in detail. It is to be understood, however, there is no intention to limit the invention to the particular form disclosed. On the contrary, it is intended that the invention cover all modifications, equivalences and alternative constructions falling within the spirit and scope of the invention as expressed in the appended claims. Although only one embodiment of the product end-items, viz., packages, produced by the instrumentation is shown in the drawings, it is to be likewise understood that there is no intention to limit packages to the particular form disclosed.

To facilitate understanding of the present invention vis-a-vis the instrumentation disclosed in my '365 patent, reference numbers used there are used here where an element or indium is unmodified or modified but functionally the same.

Figure 1A:
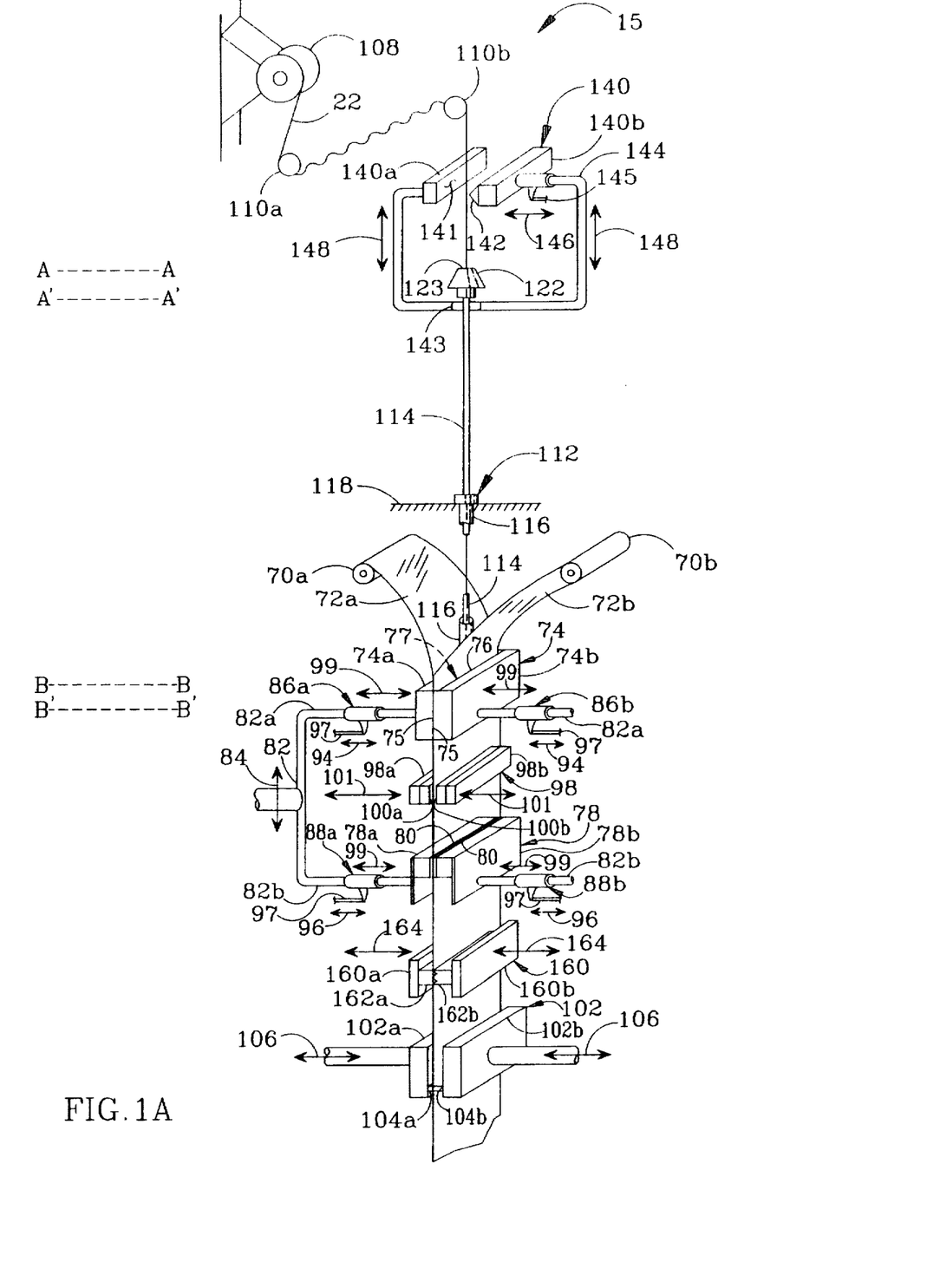
FIG. 1A is a perspective view of a package-forming instrumentation including a gripper assembly and a feed tube/piston which move vertically in unison, and a second horizontal sealing mechanism, and showing the relative spatial relationship therebetween when the gripper and feed tube/piston are at their uppermost position.
Figure 1B:
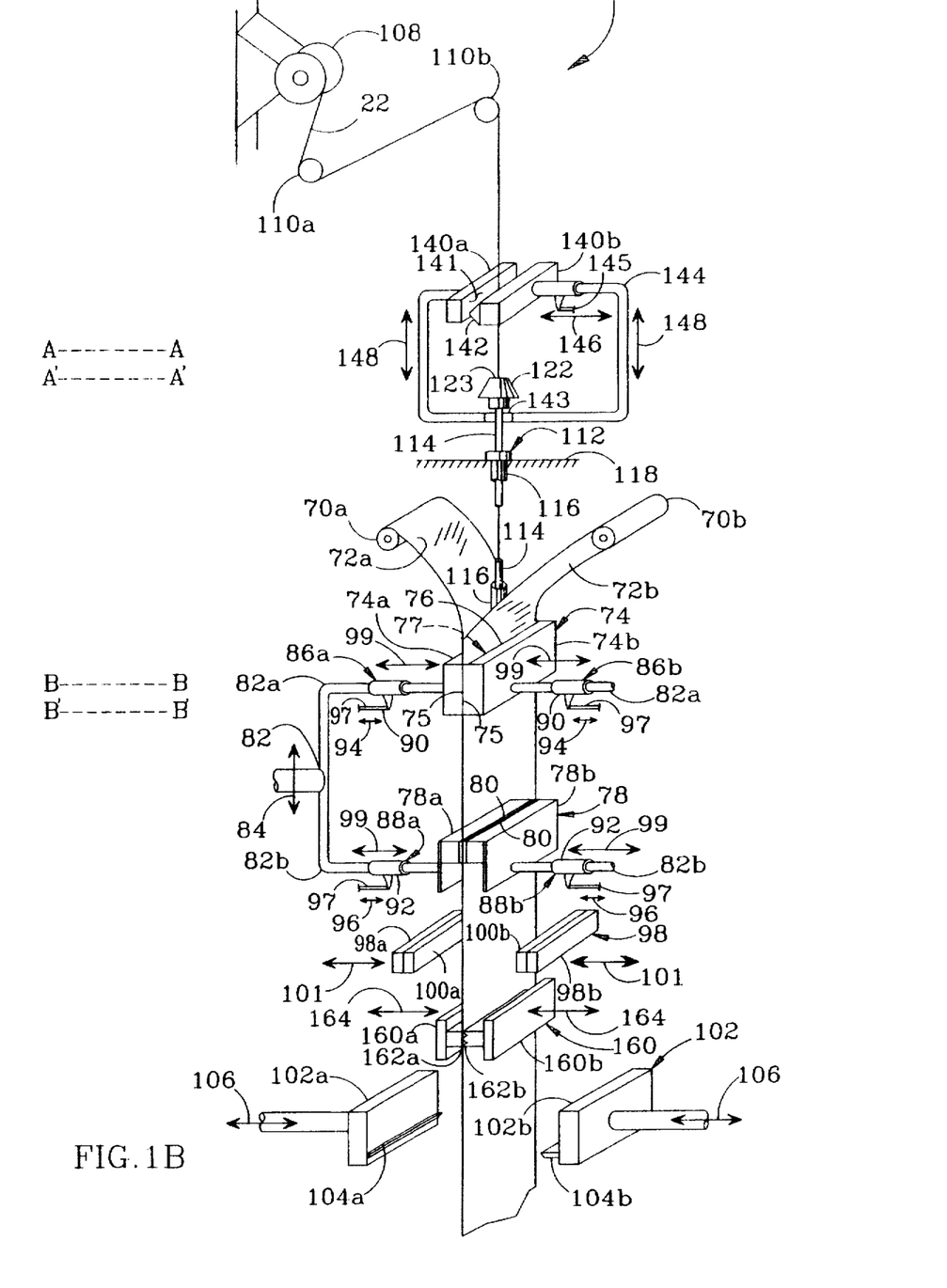
FIG. 1B is a perspective view of the FIG. 1A instrumentation when the gripper and feed tube/piston are at their lowermost position.

Referring to FIGS. 1A and 1B, a packaging instrumentation 15 includes two rolls or sources 70a and 70b of film wrapping material 72a and 72b, each of which may comprise either a single layer of polyethylene or a laminate of an inner layer of polyethylene and an outer layer of any suitable material such as paper or aluminum. Alternatively, a single roll may be used, the film sheeting passing over a guide that folds it double, whereupon the fold seams are slit to form two sheets that can be accurately aligned to maintain "registration" between writing and indicia imprinted on the two sheets. Polyethylene is preferred because it is easily heat-sealable and forms a secure and sanitary package. The outer layer is selected for decorative, message bearing and/or other marketing reasons. Films 72a and 72b are guided over rollers 73 (shown in FIGS. 5–8), enabling them to be fed within a vertical sealing mechanism 74 comprising mating halves 74a and 74b. Each half includes a pair of vertical, parallel extending contactable faces 75 separated by a vertical channel 76. The mating channels form a vertically extending tubular recess 77, shown in a generally rectangular configuration, although other geometric shapes are acceptable, provided that a through opening results. Contactable faces 75 of the mating halves may have interfitting ridges and grooves so that when sealing mechanism 74 is heated and films 72a and 72b are pressed between the vertically extending faces, the entrapped inner layer of the films are sealed together at their edges but not at their centers, as permitted by recess 77, to form side seals such as seals 26a and 26c of FIGS. 5A, 6A and 10.

Positioned below vertical sealing mechanism 74 is a holder mechanism 78 comprising a pair of holder halves 78a and 78b, which include resilient pads 80 of elastomeric material. Each half of sealing mechanism 74 and of holder mechanism 78 is movable towards and away from one another by paired, linearly movable mechanisms 86a–86b and 88a–88b, respectively, as indicated by double-headed arrows 99. Sealing mechanism 74 and holder mechanism 78 are connected by a coupling 82 which moves respective sealing halves 74a and 74b and holder halves 78a and 78b up and down in unison, as represented by double-headed arrow line 84, between an uppermost position B—B and a lowermost position B'—B'. The separation between the two positions, typically two to four inches, corresponds to the vertical height of the packages being formed. Sealing mechanism halves 74a and 74b and holder mechanism halves 78a and 78b are slidably mounted on respective arms 82a and 82b of coupling 82. Mechanisms 86a–86band 88a–88b include respective slidable sleeves 90 and 92 on arms 82a and 82b which couple the mechanism halves 74a–74b and 78a–78b to arms 82a and 82b to permit horizontally rectilinear movement of vertical sealing mechanism 74 and holder mechanism 78 with respect to one another and to coupling 82, as denoted by indicia 94 and 96. Preferably, mechanisms 86a–86b and 88a–88b comprise a hydraulic piston having one end secured to coupling 82a and 82b and the other end to sealing mechanism 74 and holder mechanism 78 through a plurality of links 97.

Positioned below sealing mechanism 74 is a first horizontal sealing mechanism 98 comprising sealing halves 98a and 98b which are disposed to move only towards and away from one another, as represented by double-headed arrow lines 101. Each half 98a, 98b includes a horizontally disposed sealing platen 100a, 100b, respectively, which, when heated and pressing films 72a and 72b together, simultaneously form top and bottom seals, such as seals 26b and 26d of FIGS. 5A, 6A and 7A, but of successive packages. When coupled mechanisms 74 and 78 are in their lowermost position (see FIG. 1A), mechanism 98 is disposed between mechanisms 74 and 78. When mechanisms 74 and 78 are in their uppermost position (see FIG. 1B), mechanism 78 is disposed slightly above mechanism 98.

A holding-and-cutting mechanism 102 is positioned below holder mechanism 78. Mechanism 102 includes a pair of holder halves 102b and 102b to which are attached, respectively, knife edges 104a and 104b. The halves 102b, 102b are constrained to move towards and away from one another as represented by double-headed arrow lines 106. Thus, when the halves move towards one another to grip a section of completed packages still attached to other packages, some of which are still in process of completion, knife edges 104a and 104b separate the lowermost package from the remaining packages.

Figure 10:
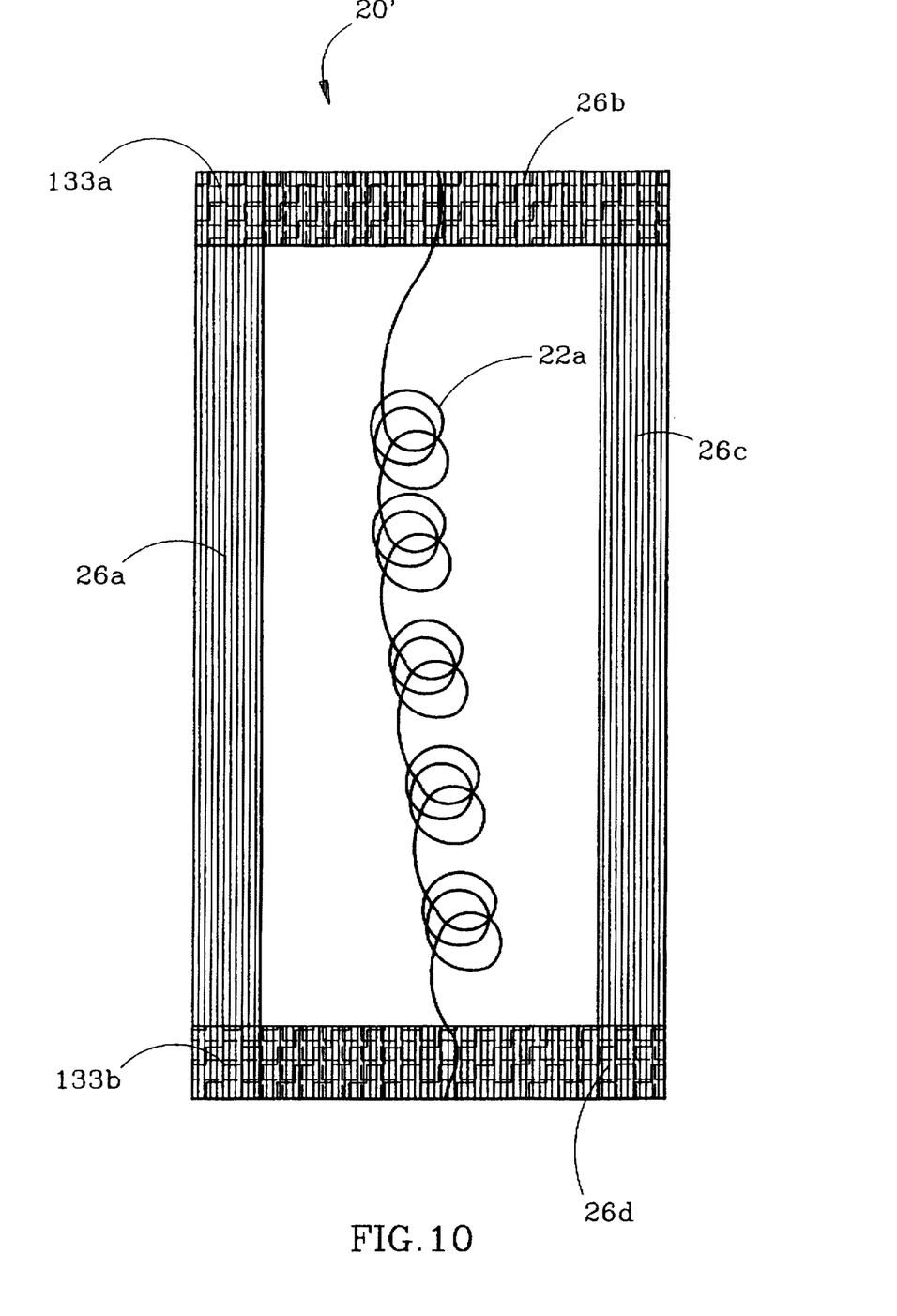
FIG. 10 shows a hermetically sealed package enclosing a filament, produced by the FIGS. 1A, 1B instrumentation, wherein the opposite ends of the filament are disposed within the peripheral seal of the package.

Positioned between holder mechanism 78 and holding and-cutting mechanism 102 is a second horizontal sealing mechanism 160 comprising sealing halves 160a and 160b which are disposed to move only towards and away from one another, as represented by double-headed arrow lines 164. Each half 160a, 160b includes a horizontally disposed sealing platen 162a, 162b, respectively, which, when heated and pressing against contiguous top and bottom seals of successive packages, such as seals 26b and 26d of FIGS. 5A, 6A and 7A, superimpose, as shown in FIG. 10, seals 133a, 133b over the existing horizontal seals.

Still referring to FIGS. 1A and 1B, a flaccid filament 22 such as dental floss is supplied from a spool or bobbin 108 as a continuous, uncut length, which is extended about first and second guiding rollers 110a, 110b, respectively, into a feeding mechanism 112. The feeding mechanism comprises a feed tube 114 and a tubular mandrel 116, which are concentric and relatively movable with respect to one another. Preferably, feed tube 114 is movable and mandrel 116 is fixed to a support 118. Recess 77 of vertical sealing mechanism 74 is wider than mandrel 116 and therefore extends about and preferably is not in contact with the mandrel. A collar 122 is affixed to the upper end of feed tube 114 and is provided with an upper guiding surface 123 having the general shape of a half doughnut, to provide a rounded annular entry for the filament 22.

Figure 2A:
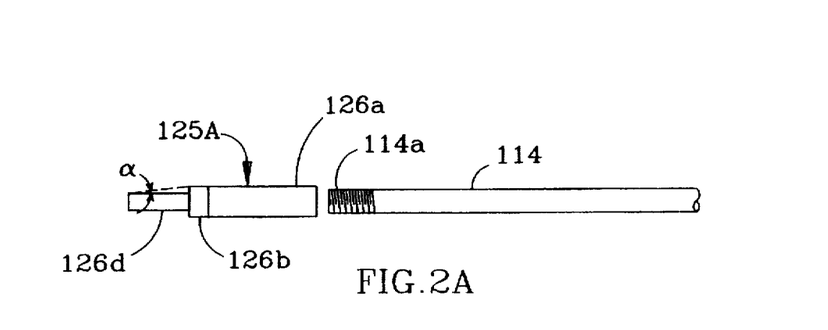
FIG. 2A is an exploded view of a first embodiment of a piston according to the present invention, connected to the lower end of the feed tube of the '365 and '221 references.
Figure 2B:
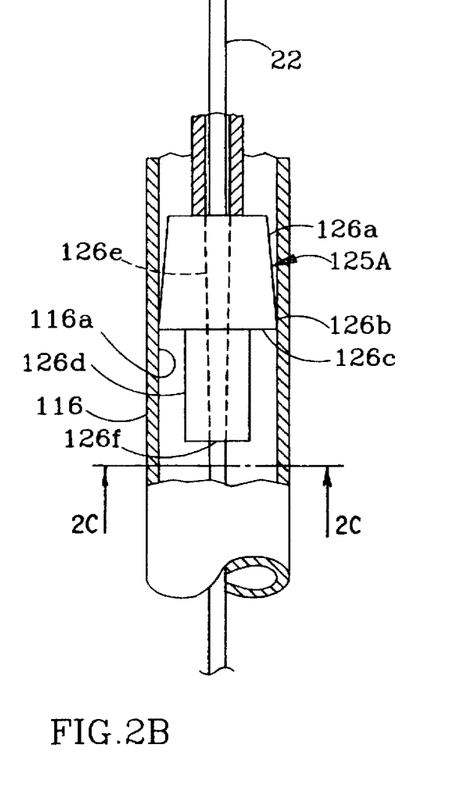
FIG. 2B is a cross-sectional view of the FIG. 2A piston connected to the feed tube lower end and disposed within the '365/'221 mandrel.
Figure 2C:
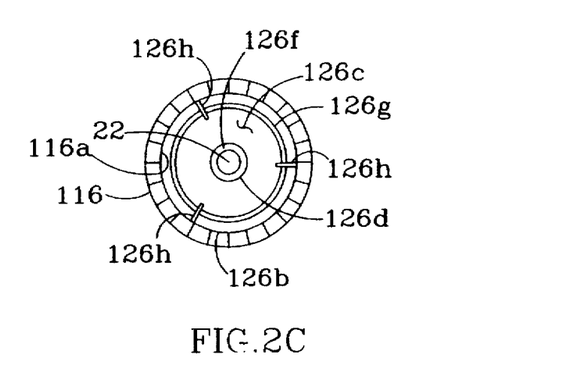
FIG. 2C is a three-dimensional plan view with respect to a plane depicted by line C—C in two-dimensional FIG. 2B.

As shown in FIG. 2A, feed tube 114 is terminated at its lower end 114a by a piston 125A. The piston is threaded, bonded or otherwise affixed to feed tube end 114a so that the feed tube and piston move together within mandrel 16. As shown in FIGS. 2A, 2B and 2C, the piston 125A includes a slightly tapered upper portion 126a with a lowermost outer cylindrical surface 126b closely received and slidable within the mandrel, and a generally planar lower end surface 126c. Piston 125A further includes a lower portion 126d tapered at an angle α of about 1 degree. As shown in FIG. 2B, a tapered bore 126e extending through piston 125A has a diameter at the top of portion 126a about that of the feed tube inner diameter, typically 0.100-inch, and a diameter at the bottom end of portion 126d slightly larger than the filament diameter and terminating in an exit hole 126f through which filament 22 is threaded. Typically, bore 126e tapers to a hole having a diameter in the range 0.008 to 0.012-inch larger than the filament 22 so that the narrowest bore segment and exit hole exert a frictional hold on the filament segment within the piston portion 126d sufficient to prevent the filament from backing up into the piston and feed tube as the piston is pushing the filament segment extending beyond hole 126f into a package compartment. It is essential that the bore be kept free of dirt and product residue; otherwise, the filament will jam in the bore and become stretched, and the instrumentation will not function properly. Surface 126b of piston portion 126a is in slidable contact with inner surface 116a of mandrel 116 due to a close interfit between the two surfaces. Referring to FIG. 2C, the surface 126c includes a circumferential groove 126g transected by a plurality (typically, three) of radial grooves 126h. As piston 125A repeatedly slides up and down, surface 126b rubs against surface 116a. Were piston portion 126A rigid, surface 126b would soon wear down, creating a crevice into which filament could lodge, thereby jamming the instrumentation. Grooves 126g, 126h mitigate erosion by enabling surface 126b to flex continually when the piston moves. To minimize friction, piston 125A preferably is formed from an annealed copolymer acetal or an equivalent composition, while feed tube 114 and mandrel 116 are preferably metallic, e.g. of stainless steel or the like. In the preferred embodiment, the length of mandrel 116 is 24-inches and the combined length of feed tube 114 and piston 125A is 30-inches. The piston stroke is adjustable. In the preferred embodiment, piston 125A is fabricated from POLYPENCO ACETRON™, available commercially from Polymer Corporation of Reading, Pa.

Figure 2D:
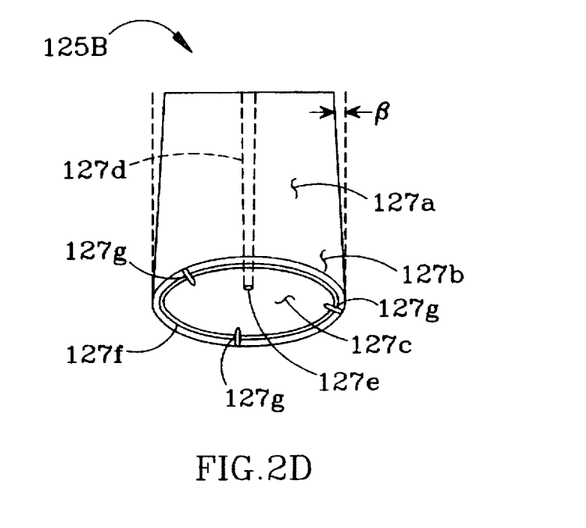
FIG. 2D is a perspective view of a second piston embodiment.

Referring to FIG. 2D, a piston 125B which is an alternative to piston 125A includes a surface 127a rotationally symmetric about a longitudinal axis and tapered upwardly at an angle β of about 1 degree, and terminating in a cylindrical lower surface 127b in slidable contact with mandrel surface 116a. Piston 125B further includes a generally planar bottom end surface 127c and a bore 127d tapered as in piston 125A, i.e., from a maximum diameter at the piston top about that of feed tube 114 to a minimum diameter at an exit hole 127e slightly larger (e.g., 0.010-inch) than the filament diameter. Surface 127c includes an annular groove 127f transected by a plurality (typically, three) of radial grooves 127g. Grooves 127f, 127g act to mitigate erosion of surface 127b in the same manner as do grooves 126g, 126h. Piston 125B is fabricated from the same material as piston 125A.

Referring again to FIGS. 1A and 1B, the instrumentation 15 further includes a gripper assembly 140 rigidly connected at a junction 143 to feed tube 114 by a bracket 144, the combination of gripper assembly, bracket, feed tube and piston being movable up and down, as represented by double-headed arrow lines 148, between an uppermost position A—A and a lowermost position A'—A'. The gripper-tube-piston combination moves opposite to the combination of sealing mechanism 74, coupling 82 and holder mechanism 78, so that when one combination is at its uppermost position the other combination is at its lowermost position. In the currently preferred embodiment, the distance between A—A and A'—A' is twenty inches while the distance between B—B and B'—B' is three inches. Thus, in cycling up-and-down, the gripper-tube-piston combination moves about seven times faster than the vertical sealer coupling-holder combination.

Figure 3:
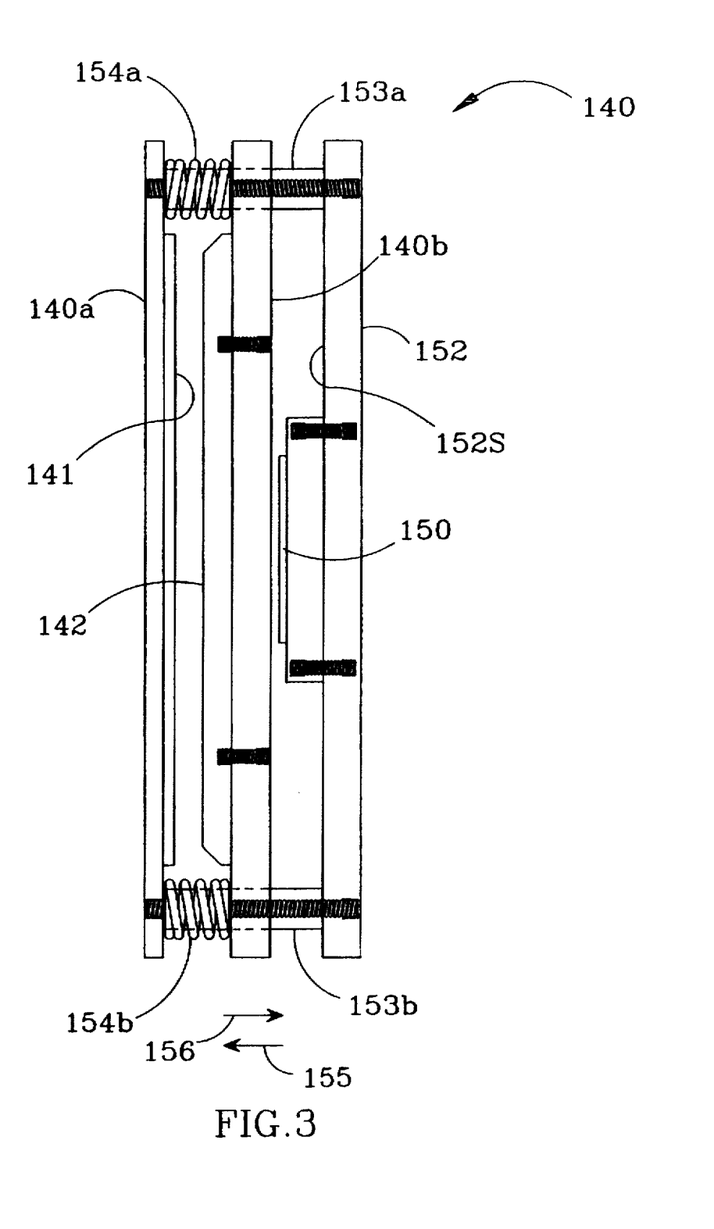
FIG. 3 is a top plan view of the FIGS. 1A, 1B gripper assembly.

Gripper assembly 140 includes opposed portions 140a and 140b, the portion 140a being immovable horizontally and including a generally vertical planar surface 141, and the portion 140b including a "V"-shaped surface 142 and being movable toward and away from portion 140a via a linearly movable mechanism 145, as represented by double-headed arrow line 146. Referring to FIG. 3, in the preferred embodiment the mechanism 145 is a pneumatically operated piston 150 rigidly connected to a mounting plate 152 at a surface 152S proximate to portion 140b. Mounting plate 152 and portion 140b are separated by opposed rigid spacers 153a and 153b. Portion 140b is adjustably separated from portion 140a by opposed spring-mounted compressible spacers 154a and 154b. Activating piston 150 by applying air pressure causes the piston to press against portion 140b so that spacers 154a, 154b compress until the V-shaped surface 142 contacts surface 141 of portion 140a, as represented by single-headed arrow line 155, thereby immobilizing the portion of filament 22 below the gripper assembly 140. Deactivating piston 150 by shutting off the air pressure causes the spacers 154a, 154b to return to their unstressed position, as represented by single-headed arrow line 156, creating a gap between surfaces 141 and 142, thus releasing the filament 22. In the preferred embodiment, piston 150 is a diaphragm piston having a stroke of about 3 mm.

Figure 4:
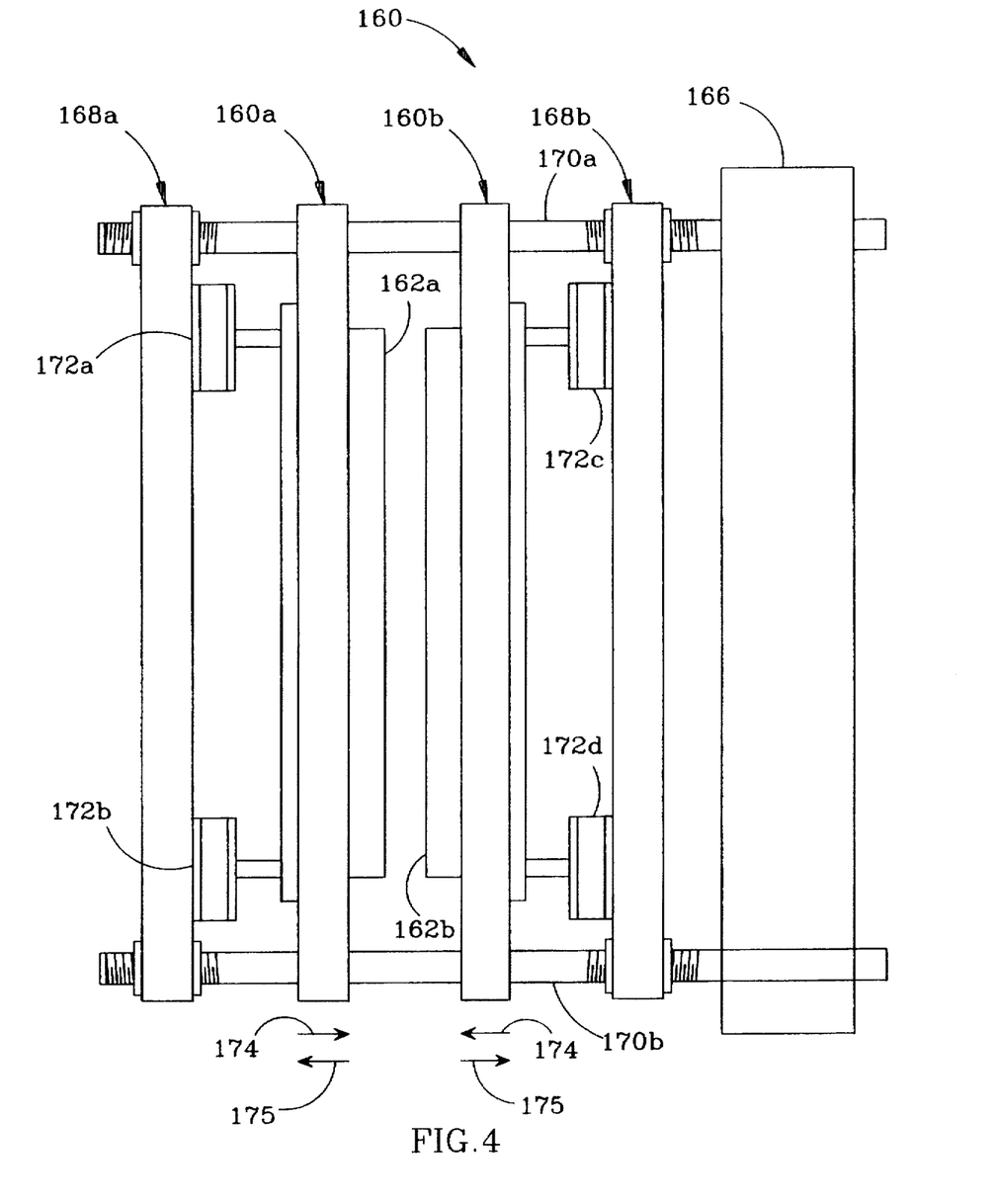
FIG. 4 is a top plan view of the FIGS. 1A, 1B second horizontal sealing mechanism.

Referring to FIG. 4, the second horizontal sealing mechanism 160 includes a base plate 166 rigidly connected to first and second mounting plates 168a, 168b by opposed rods 170a, 170b transverse to plates 166, 168a, 168b. Opposed pneumatic pistons 172a, 172b and 172c, 172d, respectively, are rigidly connected between plate 168a and sealing half 160a, and between plate 168b and sealing half 160b, respectively. Sealing halves 160a and 160b are slidably movable along rods 170a and 170b. Thus, when pistons 172a, 172b, 172c, 172d simultaneously extend, the sealing platens 162a and 162b move toward each other, as represented by single-headed arrow lines 174. When the pistons simultaneously retract, the sealing platens move away from each other, as represented by single-headed arrow lines 175.

Figure 5:
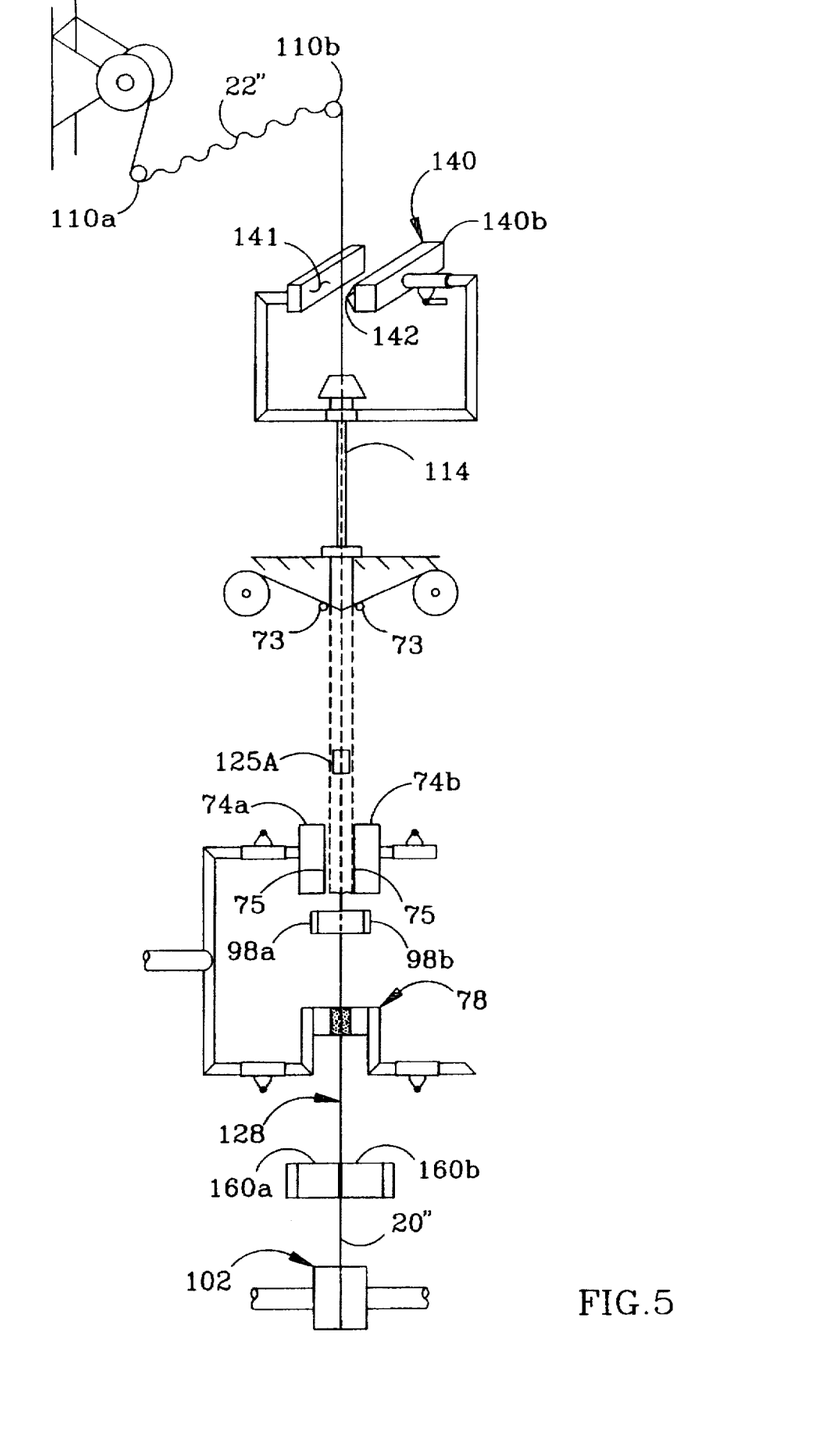
FIG. 5 is a simplified diagrammatic view of a process step wherein the instrumentation is in the FIG. 1A configuration.
Figure 5A:
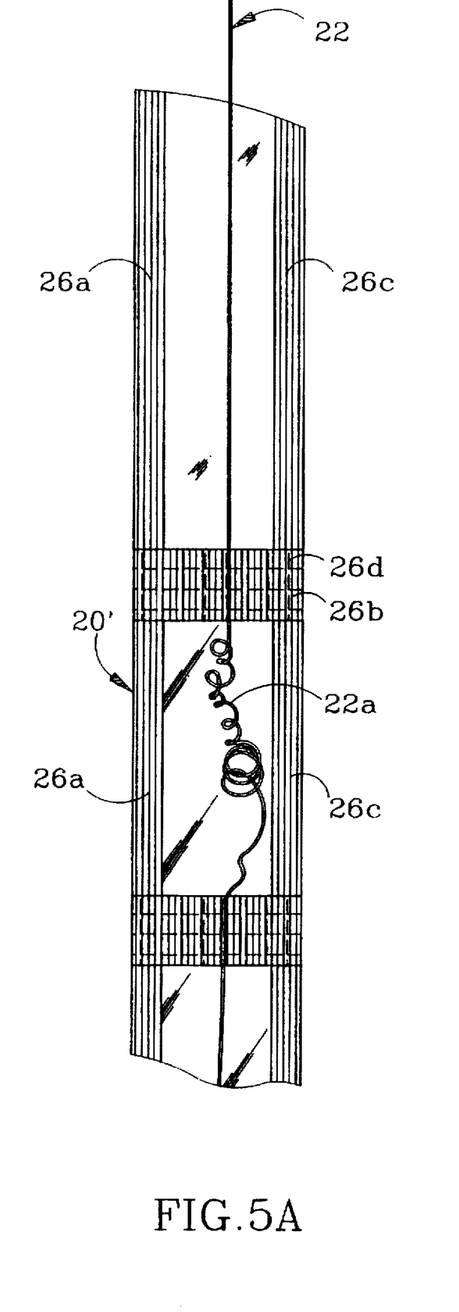
FIG. 5A shows two contiguous in-process packages in relation to the respective filament segment each encloses during the FIG. 5 step.
Figure 6:
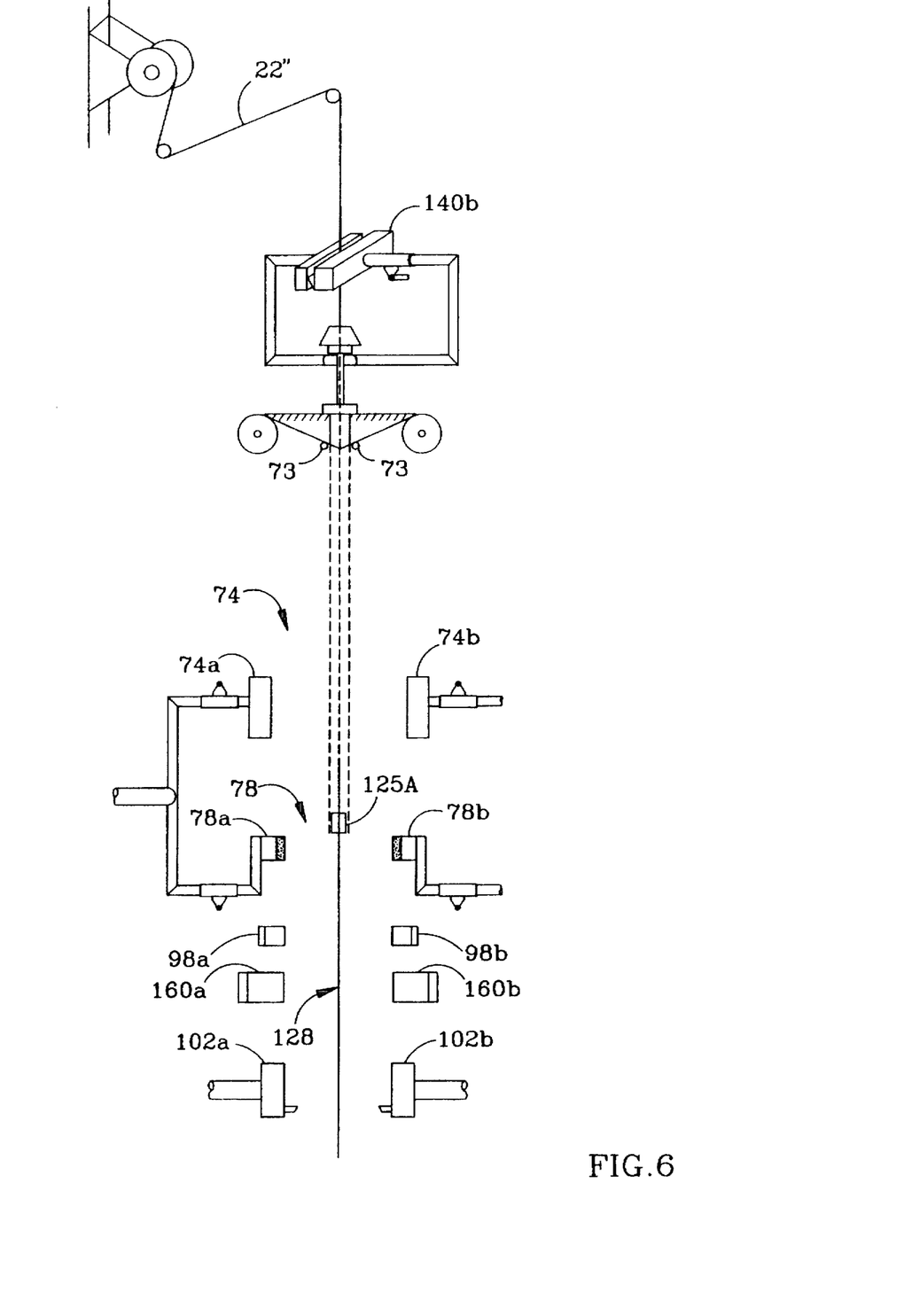
FIG. 6 is a simplified diagrammatic view of a process step following the FIG. 5 step wherein the FIGS. 1A, 1B gripper and feed tube/piston are at their lowermost position and the second horizontal sealing mechanism is open.
Figure 6A:
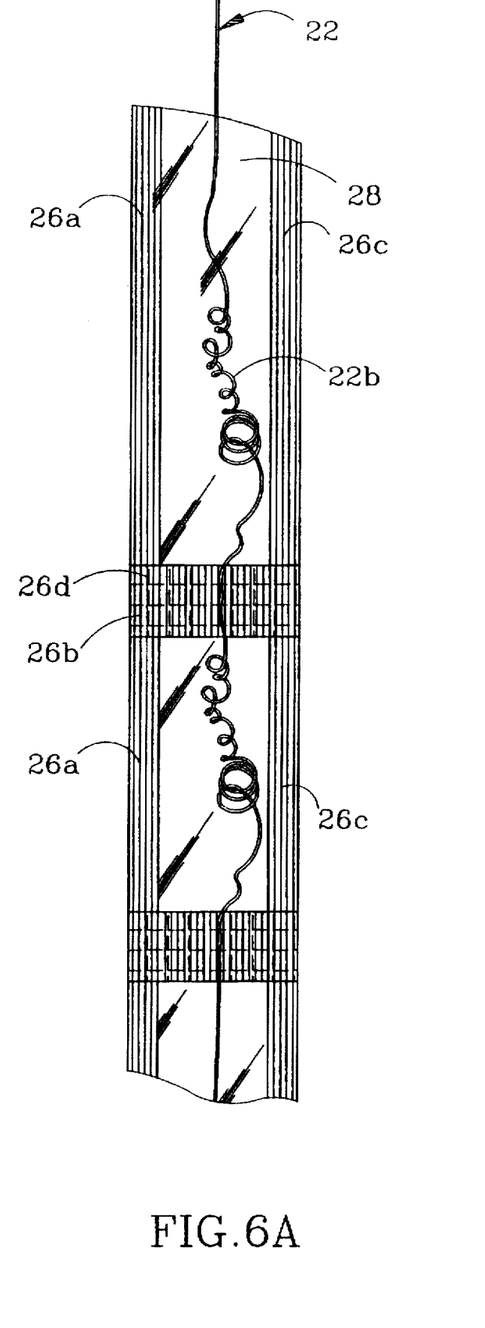
FIG. 6A shows the FIG. 5A packages and filament segments during the FIG. 6 step.
Figure 7:
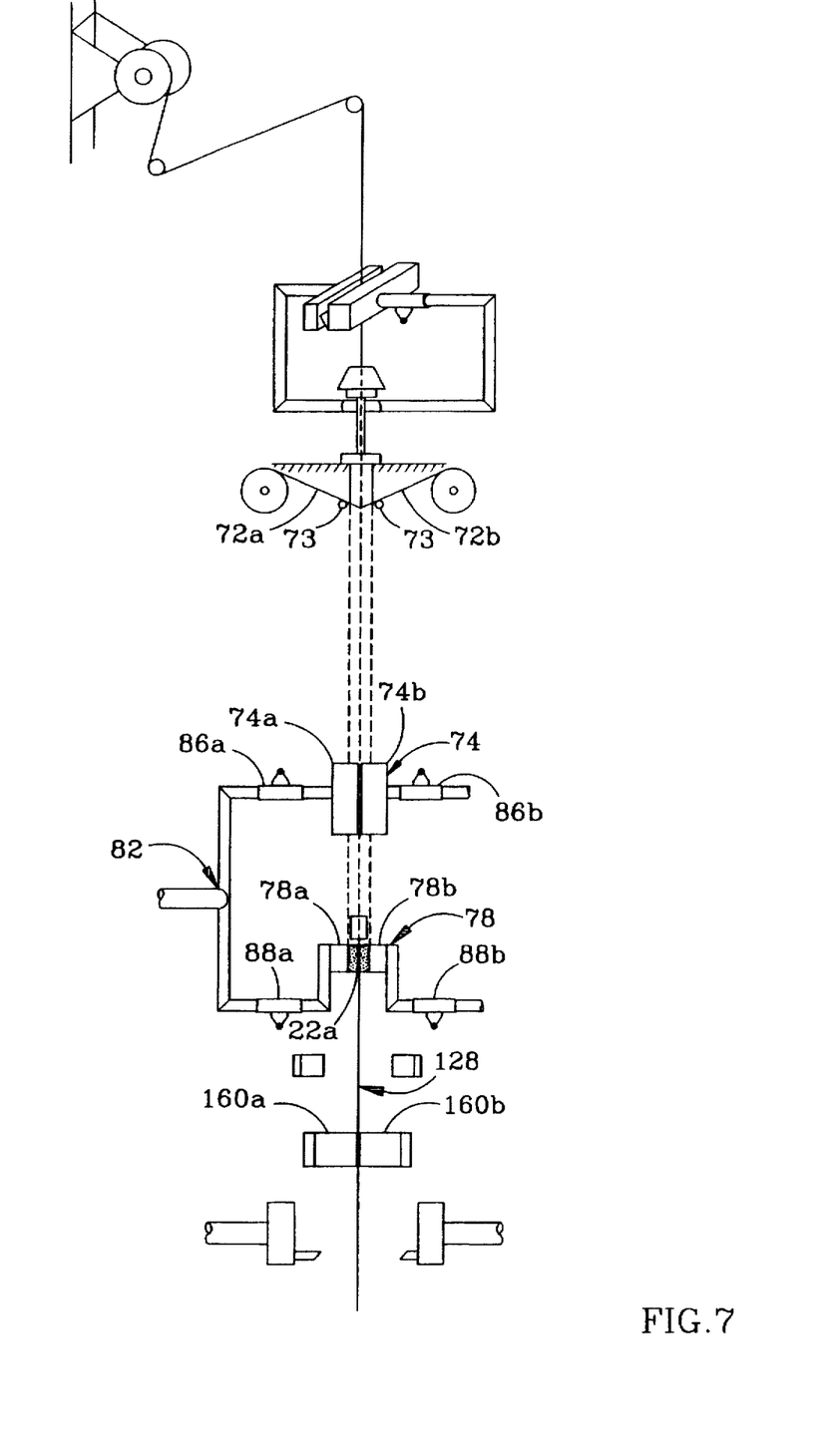
FIG. 7 is a simplified diagrammatic view of a process step following the FIG. 6 step wherein the instrumentation is in the FIG. 1B configuration.
Figure 7A:
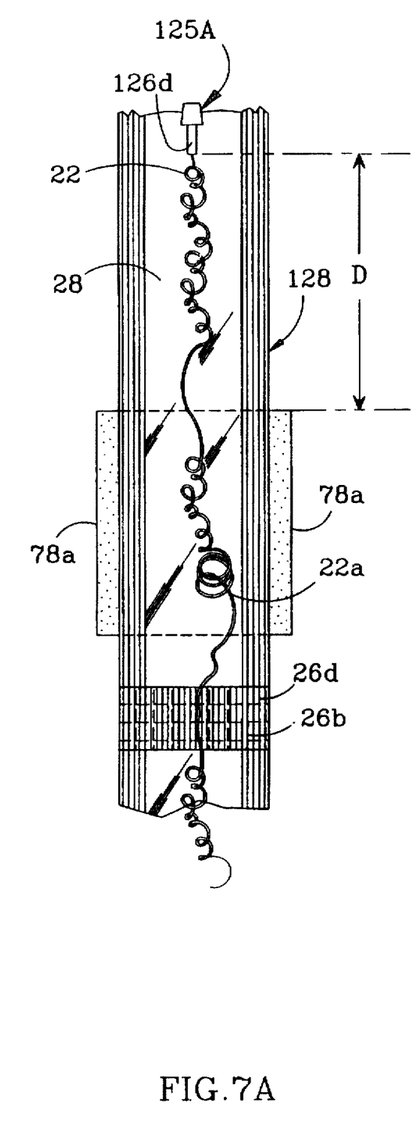
FIGS. 7A and 7B show the FIGS. 2A–2C piston and a filament segment in relation to an in-process package during the FIG. 7 step.

The sequence of process steps executed by the instrumentation 15 is illustrated in FIGS. 5–8, with further reference to a strip of packages in formation, designated by indicium 128 in FIGS. 5A, 6A, 7A,, 7B, 9A, 9B. Strip 128 is shown in diagrammatic edge view in FIGS. 5–8 and 9A, and in full side view in FIG. 9B. Thus, the FIGS. 5–8 and 9A view, in its simplified representation, does not illustrate the thickness of package strip 128 nor the bulging out of wrapping material 72a and 72b.

As shown in FIG. 5, one or more packages 20" have already been completed and are about to be separated by cutter blades 104a (not shown), 104b (not shown) of holding-and-cutting mechanism 102 from the remainder of the packages in strip 128 in production, with mechanism 102 in pressing contact with strip 128. Also, the platens 10a (not shown), 100b (not shown) of first horizontal sealing mechanism halves 98a and 98b are in pressing contact with strip 128 to form, as shown in FIG. 5A, contiguous bottom and top seals 26d, 26b, respectively, of successive leading and trailing packages. Piston 125A, feed tube 114 and gripper assembly 140 are at their uppermost position (A—A in FIG. 1A), the piston having pushed downward, during the previous process cycle, a bunched-up segment 22a of filament 22 which was deposited within package 20'. That amount of filament, together with package strip 128, was grabbed by holder mechanism 78 and pulled downward as mechanism 78 descended to its lowermost position (B'—B' of FIG. 1A). As illustrated in FIG. 5 by indicium 22", the filament segment passing over rollers 110a, 110b is slack, in preparation for being pulled downward in a subsequent step.

As further shown in FIG. 5, vertical sealing mechanism halves 74a and 74b are in pressing contact with package strip 128. While coupled mechanisms 74 and 78 are moving downwardly from their uppermost position (B—B in FIG. 1A) to their lowermost position shown in FIG. 5, faces 75 of mechanism 74 are forming side seals. Also, platens 162a (not shown) and 162b (not shown) of second horizontal sealing mechanism halves 160a and 160b, respectively, are in pressing contact with strip 128 to form a second seal 133 (see FIG. 10) over contiguous top and bottom seals already formed.

In the transition of movement of instrumentation 15 from FIG. 5 to FIG. 6, gripper assembly portion 140b closes prior to descent of the gripper assembly, feed tube and piston, so that the filament is clamped between surfaces 141 and 142. As the gripper assembly moves downward, filament segment 22" becomes taut. Concurrent with transition from the FIG. 5 process step to the FIG. 6 process step, vertical sealing halves 74a, 74b, horizontal sealing halves 98a, 98b, holder halves 78a, 78b, horizontal sealing halves 160a, 160b, and holding-and-cutting halves 102b, 102b are moved back from strip 128, followed by movement upward of coupled vertical sealing mechanism 74 and holder mechanism 78 to their uppermost position (B—B in FIG. 1B). Holder halves 78a, 78b, having passed between horizontal sealing halves 98a, 98b, are now above halves 98a, 98b. As the piston descends, filament contiguous to the piston begins curling in a round wad constrained by the mandrel inner diameter. When piston 125A is used, the filament tends to curl around portion 126d. Referring to FIG. 6A, a curled-up segment 22b of filament 22 is deposited within an open compartment 28 of the next package to be sealed at its top.

Figure 7B:
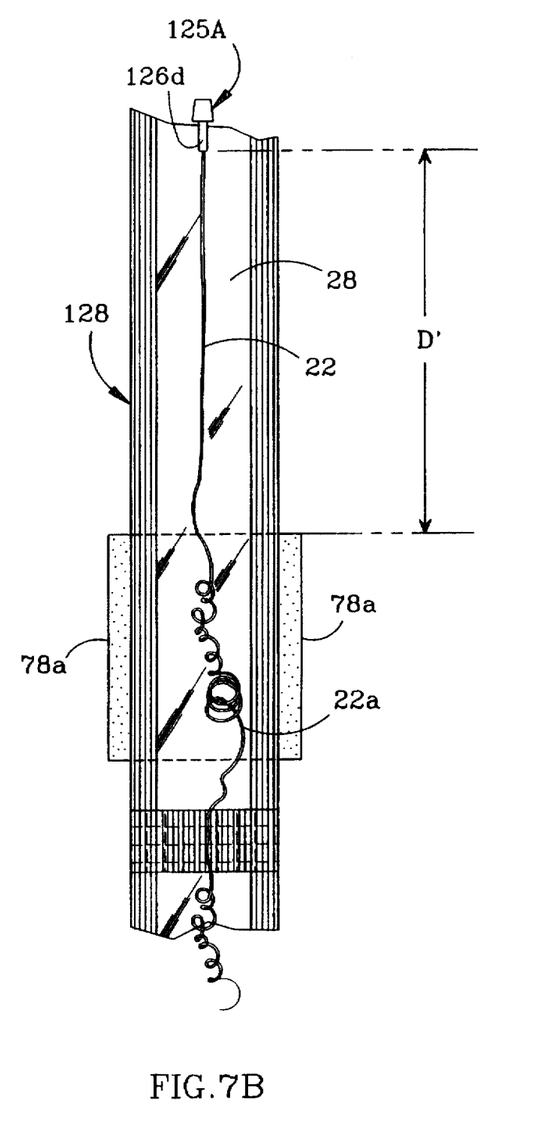

In the FIG. 7 process step, heated vertical sealing halves 74a, 74b are moved towards one another, to seal together the two films 72a, 72b to form the sealed sides 26a and 26c and open compartment 28 of the next trailing package. Immediately prior thereto, because holder 78 is slightly in advance of sealing mechanism 74, holder halves 78a and 78b grip the film material and filament portion 22a therebetween. This differential horizontal movement is effected by coordinated respective movements of mechanisms 86a–86b and 88a–88b. Coupling 82 then moves sealing mechanism 74, holder 78 and strip 128 held thereby, downwardly, from a position D with respect to the piston (see FIG. 7A) to a position D' (see FIG. 7B), thereby moving the filament portion 22 curled around piston portion 126d away from the piston. As illustrated in FIGS. 7A and 7B, this downward movement also acts to straighten the filament before it is inserted into compartment 28. Once the downward movement of coupling 82 has been effected, heated sealing halves 160a, 160b are brought into sealing contact with strip 128 to form a hermetic seal superimposed on a previously formed pair of contiguous horizontal seals. The FIG. 7 process step is illustrated in FIG. 1B.

Figure 8:
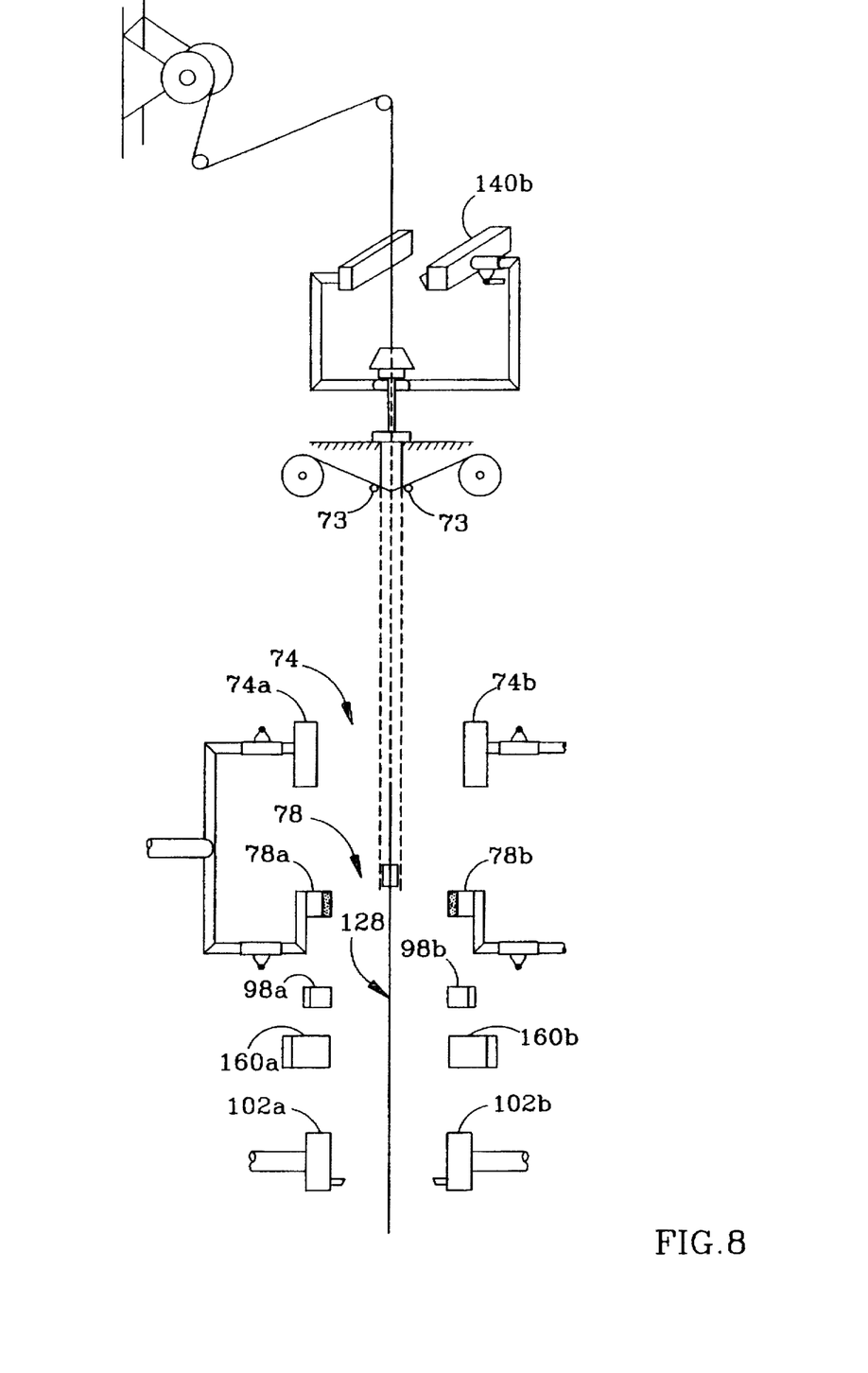
FIG. 8 is a simplified diagrammatic view of a process step following the FIG. 7 step and immediately prior to the FIG. 5 step.

In the FIG. 8 process step, vertical sealing halves 74a, 74b, horizontal sealing halves 98a, 98b, holder halves 78a, 78b, horizontal sealing halves 160a, 160b, and holding-and-cutting halves 102b, 102b all are moved back from strip 128, and gripper assembly portion 140b is retracted, preparatory to movement upward of the gripper assembly, feed tube and piston to their uppermost position (A—A in FIG. 1A), and movement downward of coupled vertical sealing mechanism 74 and holder mechanism 78 to their lowermost position (B'—B' in FIG. 1B). Thus, by the end of the FIG. 8 process step, the instrumentation is configured to transition to the FIG. 5 process step already described.

Figure 9A:
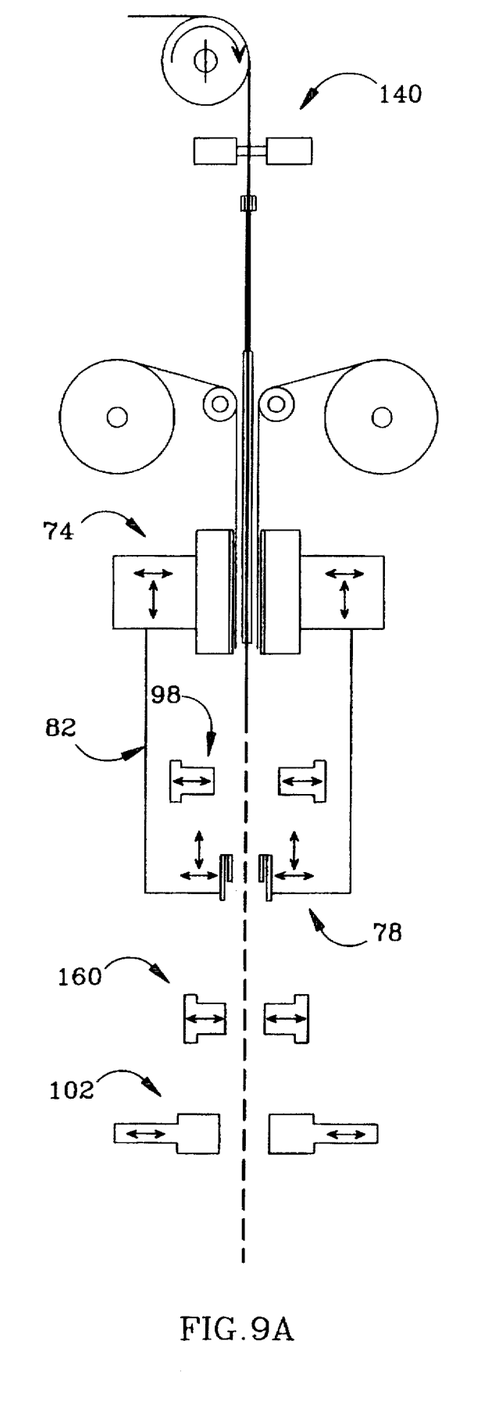
FIGS. 9A and 9B are schematic elevational views of the FIGS. 1A, 1B instrumentation in operation.
Figure 9B:
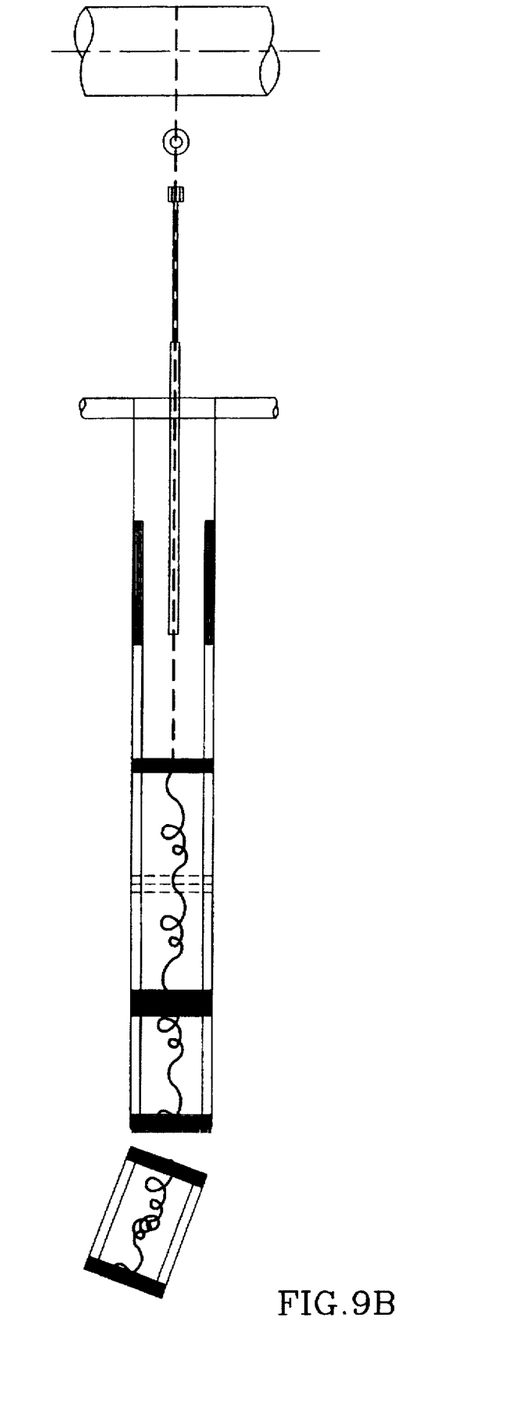

FIGS. 9A and 9B correlate the sequential steps in forming hermetically sealed packages of filament with the functions performed by the several sealing, holding and cutting mechanisms.

FIG. 10 shows a completed hermetically sealed package 20' enclosing a filament segment 22a, including a top seal 26b, side seals 26a and 26c, bottom seal 26d, and seals 133a and 133b superimposed, respectively, on seals 26b and 26d.

What is claimed is:

1. A heat sealed package enclosing a continuous, untangled flaccid filament comprising:
   a fully sealed enclosure comprising a compartment determined by opposed first and second continuous heat seals, and opposed third and fourth continuous heat seals generally orthogonal to the first and second heat seals and providing the sealed enclosure;
   the filament having an intermediate portion terminating in oppositely disposed end portions, with the intermediate portion being freely housed within the compartment and the oppositely disposed end portions being secured, respectively, by the third and fourth heat seals; and fifth and sixth heat seals being superimposed, respectively, on the third and fourth pre-formed heat seals for effecting hermetic seals at the interfaces of the oppositely disposed end portions of the filament and the adjacent seal areas.

2. The package of claim 1, wherein the filament includes a substance susceptible to oxidative deterioration.

3. The package of claim 2, wherein the filament is dental floss.

* * * * *